United States Patent [19]

Feldman

[11] Patent Number: 5,008,831
[45] Date of Patent: Apr. 16, 1991

[54] METHOD FOR PRODUCING HIGH QUALITY CHEMICAL STRUCTURE DIAGRAMS

[75] Inventor: Alfred P. Feldman, Columbia, Md.

[73] Assignee: The United States of America as represented by the Department of Health and Human Services, Washington, D.C.

[21] Appl. No.: 296,019

[22] Filed: Jan. 12, 1989

[51] Int. Cl.$^5$ ............................................. G06F 15/46
[52] U.S. Cl. ..................................... 364/496; 364/578
[58] Field of Search ............... 340/709, 711, 721, 789; 364/488, 491, 496, 519, 520, 522, 578, 200, 300, 900; 434/298

[56] References Cited

U.S. PATENT DOCUMENTS

| | | | |
|---|---|---|---|
| 4,476,462 | 10/1984 | Feldman | 340/711 |
| 4,593,362 | 6/1986 | Bergeron et al. | 364/488 |
| 4,704,692 | 11/1987 | Ladner | 364/496 |
| 4,747,059 | 5/1988 | Hirayama et al. | 364/496 |
| 4,855,931 | 8/1989 | Saunders | 364/499 |

OTHER PUBLICATIONS

J. Chem. Inf. Comput. Sci. (1980) "Graphical Representation of Chemical Structures in Chemical Abstracts Service Publications", A. Goodson, pp. 212-217.
J. Chem. Inf. Compute Sci. (v23, No. 2) 1983, "Heuristic Approach for Displaying Chemical Structures", C. Shelley, pp. 61-65.
Raymond E. Carhart, "A Model-Based Approach to the Teletype Printing of Chemical Structures", JCICS, 1976, pp. 82-88.

Primary Examiner—Kevin J. Teska
Attorney, Agent, or Firm—Lowe, Price, LeBlanc, Becker & Shur

[57] ABSTRACT

A computer operated method for transforming the appearance of a chemical structure entered into a computer wherein at least one alternate equivalent structure is generated within the computer (or by keyboard entry). A series of parameters applicable to chemical structures are established along with values for such parameters. Following that it is established which of such parameters are present in the first structure and the values thereof are summed to obtain a score. The parameters present in the alternate structures are then established and summed to establish a score for each. The scores are then compared and the highest score is selected and the structure corresponding to the highest score is outputted or printed.

8 Claims, 8 Drawing Sheets

METHOD FOR PRODUCING HIGH QUALITY CHEMICAL STRUCTURE DIAGRAMS

This application is related to U.S. Pat. No. 4,476,462 by the present inventor and U.S. application Ser. No. 863,981 by the present inventor filed on May 16, 1986.

TECHNICAL FIELD

This invention relates to a method for transforming the appearance of chemical structures. As chemical structures are keyed into a computer their graphic representations may be distorted. Distortions may be allowed for the sake of efficient data entry and capture. The invention comprises a computer operated method for transforming such distorted structures to conventional and aesthetically more pleasing appearance required for quality output such as printing.

BACKGROUND ART

Entering chemical structures into a computer generally constitutes a difficult task inasmuch as the conventional coding procedures are not geared to handle graphic representations. The advent of microprocessors with menu-driven graphic screens provided for more convenient coding procedures but these too were relatively slow. An improvement in this process was achieved by reducing the number of key strokes to enter two-dimensional figures such as chemical structures into a computer keyboard by utilizing contextual relationships between the character being typed at a specific location and the characters surrounding that location to predict the next character and/or location of that character to be typed. This method is described in U.S. Pat. No. 4,476,462 issued Oct. 9, 1984, to the applicant herein, the entire content of which is incorporated herein by reference. An improvement in that method is described in applicant's U.S. patent application Ser. No. 863,981, filed May 16, 1986, the entire content of which application is incorporated herein by reference.

In order to permit processing by computer, chemical structures must be converted into a suitable form, usually connectivity matrices. In this respect chemical structures are not different from other types of data, for example text, which is transposed character by character into corresponding codes.

However this is not the only transformation undergone by chemical structures. During data capture they may become distorted. Although the input operator keys into the computer what he or she perceives to be a faithful copy, that copy appears on the screen in a distorted form. This distortion is created by requirements such as that all bonds fit within multiples of character spaces and that Luhn dots represent the carbon atoms in rings. This type of distortion is not unique to chemical structures. "Shorthands" developed for taking dictation are in effect transformations undertaken to achieve speed so that the operation may be carried out in "real time".

If chemical structures arrive in a computer in a distorted form then, of necessity, another transformation is required, namely the transformation that restores the original appearance, approximates it, or perhaps even improves on it for output such as printing.

Both the connectivity matrix and the distorted input structure are available as starting points for generating an output structure. The connectivity matrix, although used by the computer for searching and recognizing structures, is not suitable for output. It constitutes a list or inventory of the atoms of a chemical structure and of the bonds connecting them. If printed as an output it is virtually incomprehensible to a chemist.

Computer programs exist that can generate graphic chemical structures from the connectivity matrix (see, for example, R. E. Carhart, JCICS, 1976, pp. 82–88). Actually, not one, but a large number of different-looking structures can be obtained from such a matrix. All are chemically correct. This is because they all are two-dimensional topological projections of a three-dimensional molecule. Of the many projections that can thus be obtained, some resemble each other but others may look quite different, so that even an experienced chemist can be misled. It is for this reason that the conventional appearance of the two-dimensional representation of a structure is important. Of the many possible depictions, the one of the most significance is the one which has become the de facto standard with which chemists are familiar.

The information necessary to represent this conventional appearance is not present in the connectivity matrix. A number of computer programs have been created to supply this information from rules derived from actual experience (see, for example, C. A. Shelley, JCICS, 1983, pp. 61–65). However experience is not easily reducible to rules and a substantial portion of the output generated by such programs fails to achieve a conventional appearance.

DISCLOSURE OF THE INVENTION

Although it may be utilized with input from other sources the method of the invention operates primarily on structures obtained with the coding process described in the applicant's U.S. Pat. No. 4,476,462 and U.S. patent application Ser. No. 863,981 referred to hereinabove.

It is a feature of the invention that distorted input structures are utilized in preference to connectivity matrices to obtain the information necessary for reconstruction of the traditional structural appearance. According to the invention it has been found that conventional structural appearance is determined by the shape and orientation of rings and chains. In traditional structures, rings may be regular or irregular; but if they are regular, their shape is stylized (see A. L. Goodson, JCICS, 1980, pp. 212–217); they are not regular polygons. Regular rings may occur in one of four major or four minor orientations. Chains tend to occur in only two shapes, namely straight or puckered, and in only the four major orientations.

In the distorted input structures rings are likely to retain their regularity or irregularity and their orientation. They are consequently amenable to conversion to conventional structures. The method of the invention proceeds in two phases. The first phase establishes which of the above parameters are present in the distorted input structure being processed. In the second phase, the distorted rings are replaced by stylized ones, retaining, if possible the same orientations.

Because of geometric constraints, it is not always possible to replace a regular distorted ring with a stylized one. If this is the case, the regular ring may have to be replaced by an irregular one. Alternatively, if an irregular ring can be changed to a regular ring, this is done.

In order to determine which rings in a multi-ring system are to be so affected, a hierarchy is established based on ring size, the number of attached rings, and the treatment of neighbor rings. This hierarchy determines the score assigned to each ring. The arrangement achieving the highest sum of these scores is selected for output.

Thus, this invention relates to a computer operated method for transforming the appearance of a first chemical structure entered into a computer as a first array, comprising storing in the computer information representative of a series of parameters applicable to chemical structures and values corresponding to the parameters, establishing which of the parameters are present in a first structure and summing its values to establish a first score and printing the structure of the first score.

In cases where alternate structures are possible the method also comprises generating within the computer at least one alternate array representative of at least one alternate equivalent of the first structure, establishing which of the parameters are present in the alternate equivalent and summing its values to establish a score for the alternate equivalent, comparing the first score and the alternate score and selecting the highese one, and printing the structure corresponding to latter highest score.

The method of the invention thus improves the appearance of the structures, not merely restoring the original appearance. Under such transformations, further, any stereochemistry implied in the drawing is retained, an important advantage in the representation of chemical structures. The method of the invention further has the capability of replacing irregular chains with regular ones.

A more complete appreciation of the invention and many of the attendant advantages thereof will be readily perceived as the same becomes better understood by reference to the following detailed description when considered in connection with the accompanying figures.

BEST MODE FOR CARRYING OUT THE INVENTION

According to the invention the distorted input structure rather than the connectivity matrix is used as a starting point for deriving the output structure. Distorted input structures have been found preferable to connectivity matrices because they retain the information necessary for the reconstruction of their traditional appearance. It has been discovered that conventional appearance is determined by the shape and orientation of rings and chains. In the distorted input structures rings usually retain their regularity or irregularity and their orientation. They are consequently usable for convesion to conventional structures.

This invention provides a computer operated method for transforming the appearance of a first chemical structure entered into a computer as a first array comprising storing in a computer information representative of a series of parameters applicable to chemical structures and values for such parameters, establishing which parameters are present in a first structure and summing its values to establish a first score and printing the structure of the first score.

The above method is suitable for the simplest structures, e.g., one atom structures. A further refinement is taught herein for more complex chemical structures. In the case of more complex chemical structures the method further comprises:

generating within the computer at least one alternate array representative of at least one alternate equivalent of said first named structure;

establishing which of the said parameters are present in said alternate equivalent and summing the values thereof to establish a score for said alternate equivalent;

comparing said first and said alternate scores and selecting the highest score; and printing the structure corresponding to said highest score.

Figure 1A:
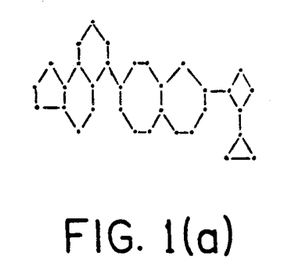
FIG. 1(a) illustrates a distorted input structure and FIG. 1(b) illustrates its stylized replacement.
Figure 1B:
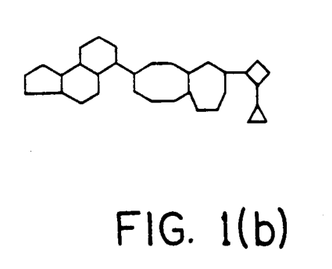
Figure 2A:
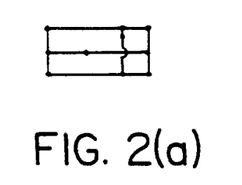
FIG. 2 illustrates at (a) and (b) different representations of adamantane which are equivalent.
Figure 2B:
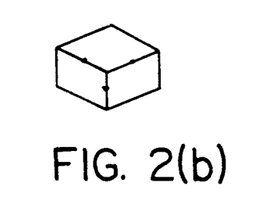

The method of the invention proceeds in two phases. The first phase establishes which of the predetermined parameters are present in the distorted input structure being processed. In the second phase the distorted rings are replaced by stylized rings retaining, as much as possible, the same orientations. Such a replacement is illustrated in FIG. 1.

Figure 3A:
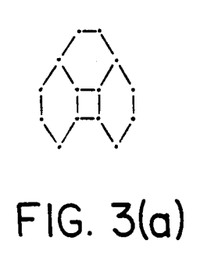
FIGS. 3(a) and (b) illustrate a distorted structure and its stylized representation.
Figure 3B:
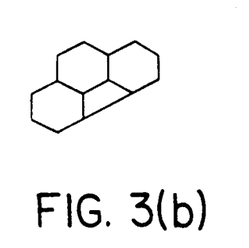
Figure 4A:
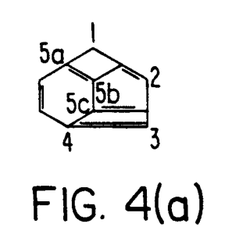
FIG. 4 illustrates how an irregular four-membered ring at 4(a) is changed to a regular one in 4(b)
Figure 4B:
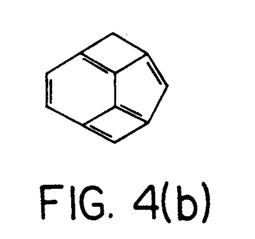
Figure 5A:
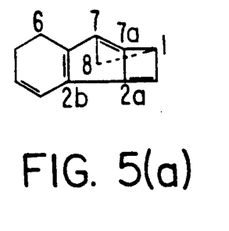
FIG. 5 illustrates an irregular four-membered structure at (a) which is changed to a regular one in (b)
Figure 5B:
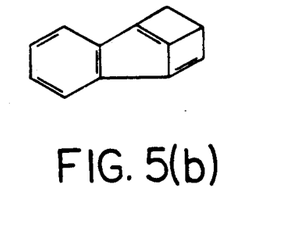
Figure 6A:
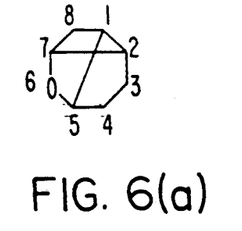
FIG. 6 illustrates a structure having only one regular ring which is changed to that illustrated at (b)
Figure 6B:
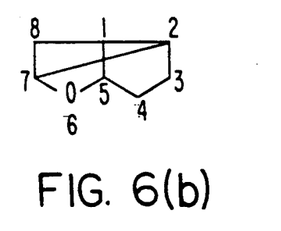
Figure 7A:
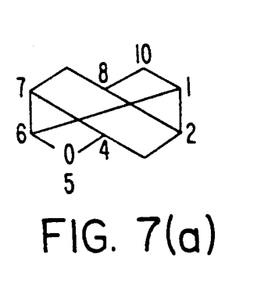
FIG. 7 illustrates at (a) a structure having no regular structure which is changed to (b)
Figure 7B:
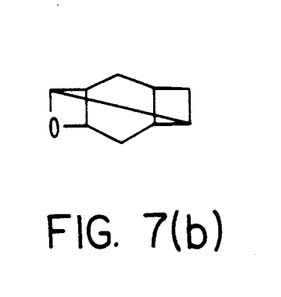
Figure 10A:
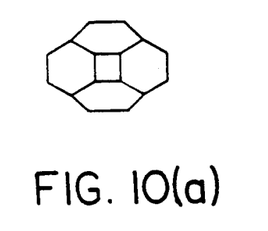
Figure 10B:
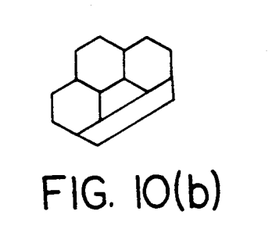

Because of geometric constraints it is not always feasible to replace a regular distorted ring with a stylized one. Where this occurs the regular ring may have to be replaced by an irregular ring as illustrated for example in FIG. 3. FIG. 3(a) represents a structure having four regular rings which may be replaced with the stylized structure illustrated at 3(b) having an irregular ring. However if the score obtained with the distorted rings (for example in FIG. 10(a) is greater than the score possible using stylized rings (for example in FIG. 10(b)) the former is retained for output. To determine which ring in a multi-ring system is to be so affected, a hierarchy is established based on ring size, the number of attached rings, and the treatment of neighbor rings. This hierarchy determines the score assigned to each ring. The arrangement achieving the highest sum of these scores is selected for output. Thus the method of the invention not only restores the original appearance but improves that appearance as is illustrated in FIGS. 4-7. Under such transformation any sterochemistry implied in the drawing is retained which is an important advantage in the representation of chemical structures.

The following table shows the parameters used according to the invention in order to determine the regularity or irregularity of structures and the method of scoring the various parameters. Some parameters will apply to each ring but in general different rings will have different mixes of parameters which are applicable. If the shape or orientation of a ring changes some parameters will also change. Each parameter is assigned a numeric value. The following Table 1 shows the values corresponding to the parameters according to one example of the application of the method of the invention:

TABLE 1

| Code | Value | Description |
| --- | --- | --- |
| A. REGULAR rings | | |
| K3 | 200 | 3-membered ring |
| K4 | 400 | 4-membered ring |
| K5 | 1000 | 5-membered ring |
| K6 | 1200 | 6-membered ring |
| K7 | 800 | 7-membered ring |
| K8 | 600 | 8-membered ring |
| B. IRREGULAR rings | | |
| I3 | 50 | 3-membered rings |
| I4 | 100 | 4-membered rings |
| I5 | 250 | 5-membered rings |
| I6 | 300 | 6-membered rings |
| I7 | 200 | 7-membered rings |
| I8 | 150 | 8-membered rings |
| C. Miscellaneous parameters | | |
| "LARGE" | −50 | PENALTY for oversize |
| "IORIENT" | −50 | PENALTY for second-best orientation |
| "ISEC" | −100 | PENALTY for SECONDARY shape |
| "ITHIRD" | −125 | PENALTY for TERTIARY shape |
| "MIXSHAP" | −275 | PENALTY for adjacent rings of same size but of different shapes |
| "KSYMM" | 250 | PREMIUM for SYMMETRY |
| "LIKE" | 1 | PREMIUM for identical orientation in both parent and revision |
| "NEIGHBOR" | 50 | PREMIUM if orientation in one ring is same as that of its NEIGHBOR (SHAPES, but not SIZES, MUST BE IDENTICAL) |

Following the assignment of values to the distorted rings the next step is to replace the distorted rings with stylized equivalents. Often more than one result may be obtained. In each instance the values of the parameters are assigned to each structure, parent as well as revisions, and these values are summed to provide a score for each structure. According to the invention the structure with the highest score is then selected. Examples illustrating the use of the method are provided below and are illustrated in FIGS. 8–19 wherein the first structure represents the input or starting structure.

Figure 8A:
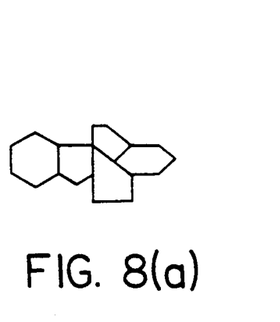
FIGS. 8-15 illustrate examples of rating or scoring structures according to the method of the invention.
Figure 8B:
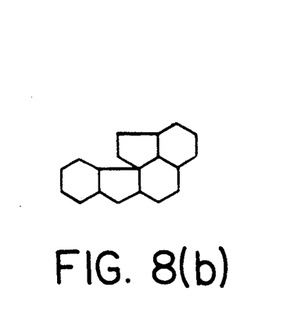
Figure 9A:
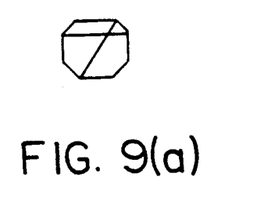
Figure 9B:
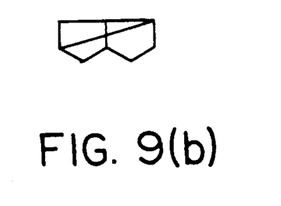
Figure 9C:
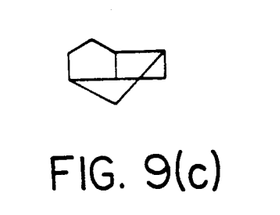
Figure 9D:
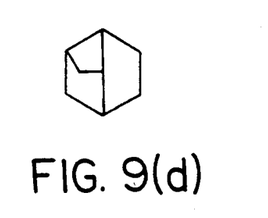

Referring to FIG. 8, Example 1 hereinbelow and the herein above Table 1, it is seen that the first structure possesses the following parameters which are scored in Table 2 hereinbelow.

TABLE 2

| Code | Value | Description |
| --- | --- | --- |
| K5 | 1000 | 5-membered ring |
| ISEC | −100 | penalty for secondary shape |
| K6 | 1200 | 6-membered ring |
| IORIENT | −50 | penalty for second best orientation |
| K6 | 1200 | 6-membered ring |
| K5 | 1000 | 5-membered ring |
| I6 | 300 | 6-membered ring |
| NEIGHBOR | 50 | premium for orientation and 1 ring same as that of its neighbor |

TABLE 2-continued

| Code | Value | Description |
| --- | --- | --- |
| Score | 4,600 | |

Structure 2 in FIG. 8 is scored utilizing the same procedure to yield the score 6,025. The score of structure 2 being the highest this structure is selected for output to the printer or otherwise.

FIG. 9 illustrating Example 2 herebelow shows that three structures 2–4 are possible as equivalents to the input structure 1. These structures are scored according to the above methodology and structure 2 is selected as having the highest score and that structure is outputted.

In Example 3 herebelow illustrated in FIG. 10 the input structure 1 has a higher score than the possible alternate structure 2 and therefore the input structure is retained for output.

Figure 11A:
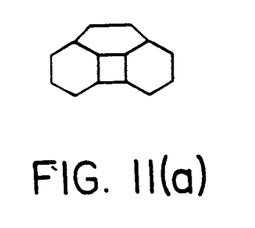
Figure 11B:
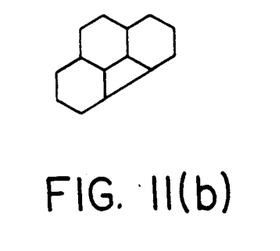
Figure 12A:
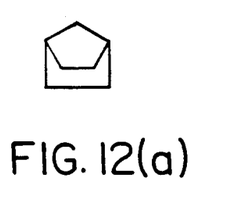
Figure 12B:
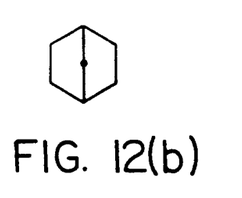
Figure 13A:
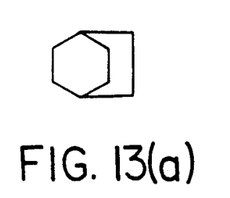
Figure 13B:
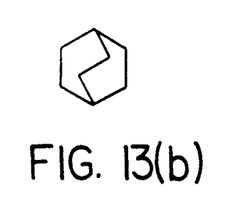
Figure 14A:
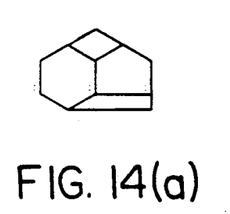
Figure 14B:
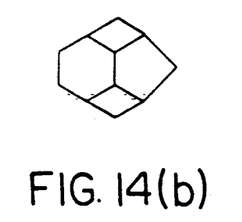
Figure 15A:
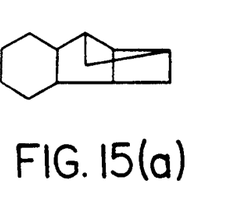
Figure 15B:
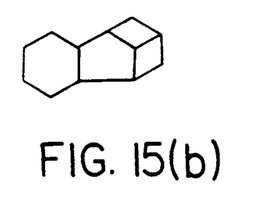

In Example 4 herebelow illustrated in FIG. 11 the alternate structure 2 carries the highest score and is selected for output.

The same analysis and selection process is carried out in the same manner with respect to the remaining Examples 5–8 included hereinbelow and illustrated in FIGS. 12–15.

Figure 16:
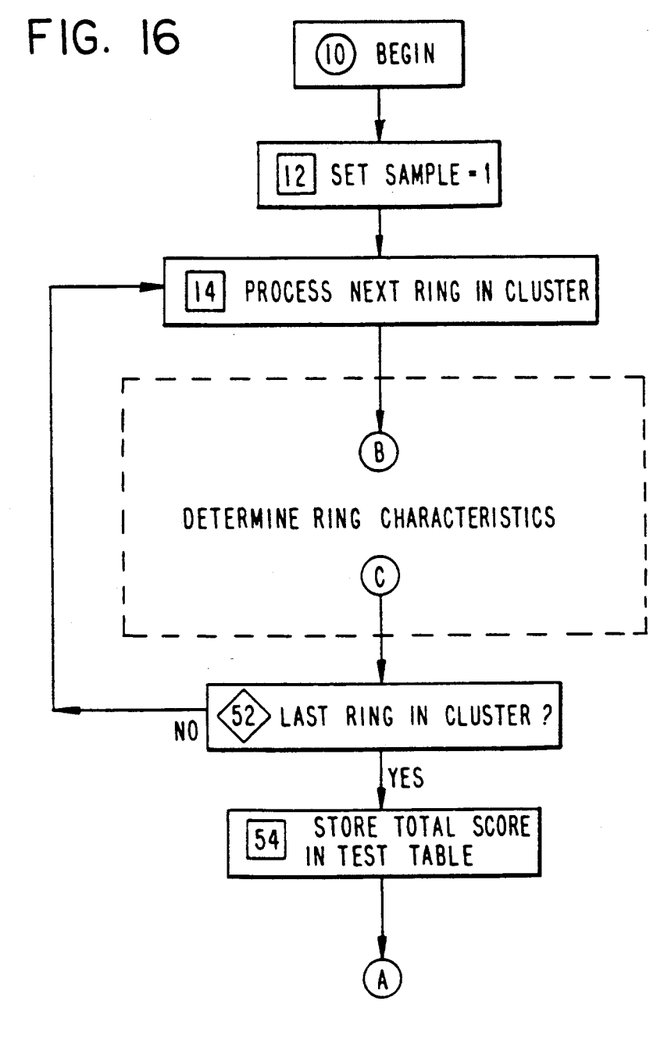
FIG. 16 is a flow diagram of the method of the invention.
Figure 17:
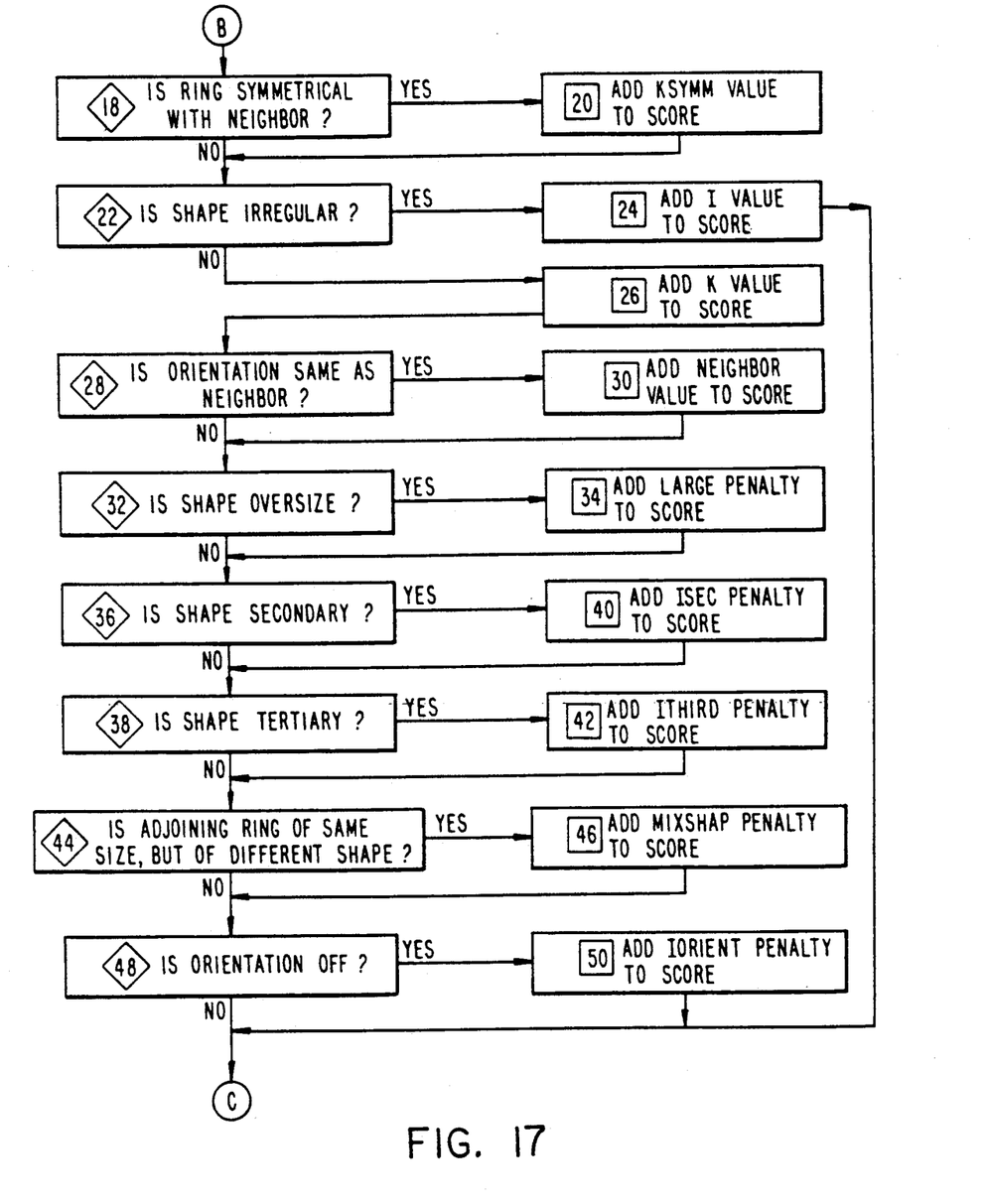
FIGS. 17 through 19 are a continuation of the flow diagram of FIG. 16.
Figure 18:
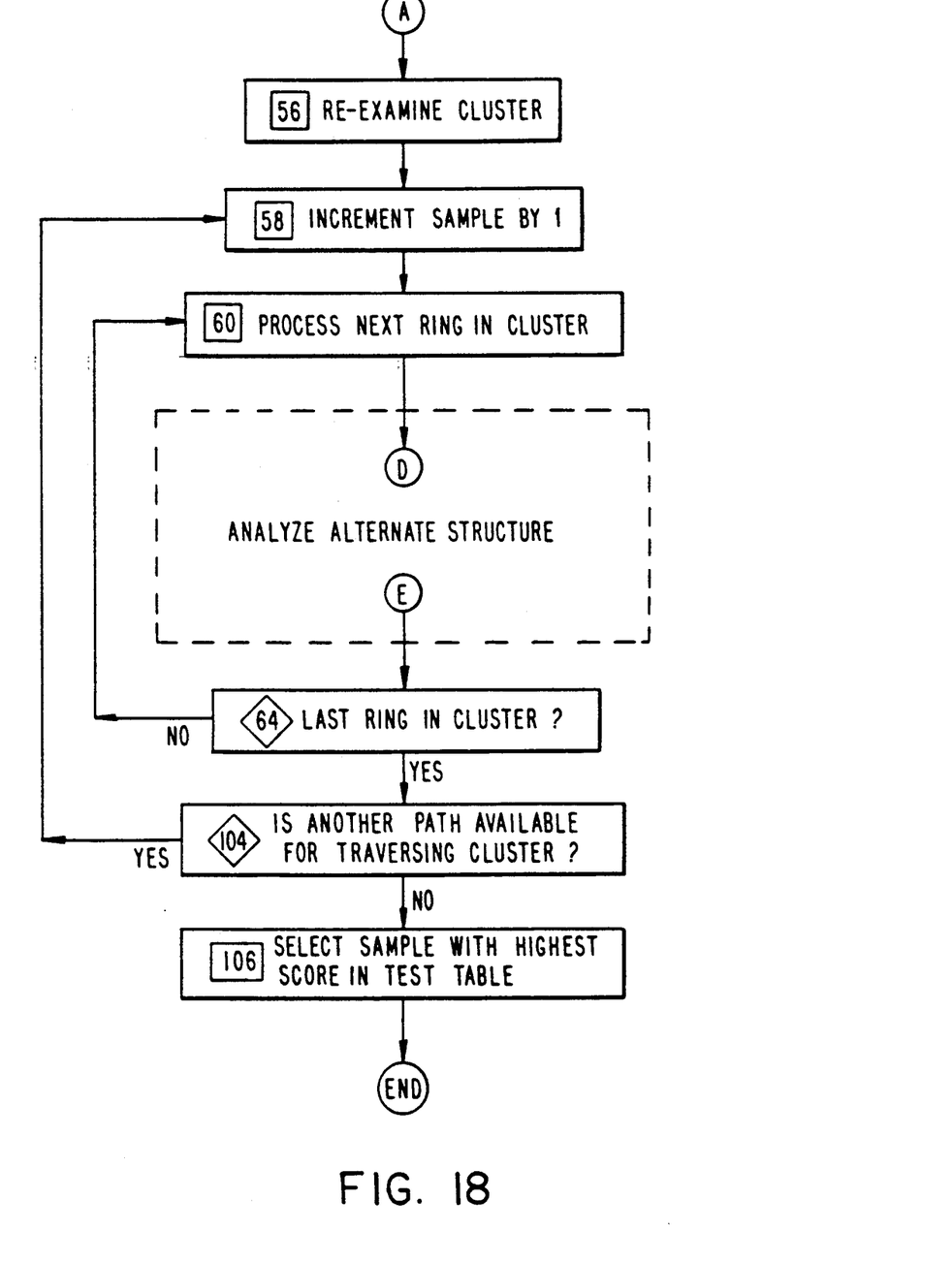

Referring to FIGS. 16 through 19 the methodology of the invention is further illustrated in diagrammatic form. FIG. 16 indicates commencement of the selection at 10 by the input at 12 of the initial distorted structure Sample 1. The first ring in the structure is processed at 14 to establish the existence thereof and to score it according to the table and as indicated for structure 1 in Example 1 in FIG. 8. The symmetry of the ring is queried at 18 (FIG. 17). If the response is affirmative the KSYMM premium for symmetry is credited to the score at 20. The regularity or irregularity of the shape of the ring is queried at 22. If the ring is irregular the appropriate I value from the Table is added to the score at 24. If the shape is regular, the response at 22 is negative, and the K value from the Table is credited to the score at 26. Orientation is queried at 28. If this is found to be the same as that of its neighbor (if any) the NEIGHBOR premium is credited to the score at 30. The size of the shape is queried at 32. If the shape is found to be oversized the LARGE penalty is added to the score at 34. The secondary or tertiary nature (if either) is queried at 36 and 38. If the shape is found to be secondary the ISEC penalty for secondary shape is added to the score at 40. If the shape is tertiary the ITHIRD penalty is added to the score at 42.

The inquiry as to different shape is made at 44 and if the answer if affirmative the MIXSHAP penalty is added to the score at 46. The orientation is queried at 48 and the IORIENT penalty added at 50 if secondbest orientation is found. The inquiry as to whether the ring examined is the last in the cluster remaining to be processed is performed at 52 (FIG. 16). If the response is negative the method proceeds back to 14 to commence processing the next ring in the cluster. When an affirmative answer is received to the last ring query the total score for that structure in the test table at 54 and the process proceeds to the next step in FIG. 18.

Figure 19:
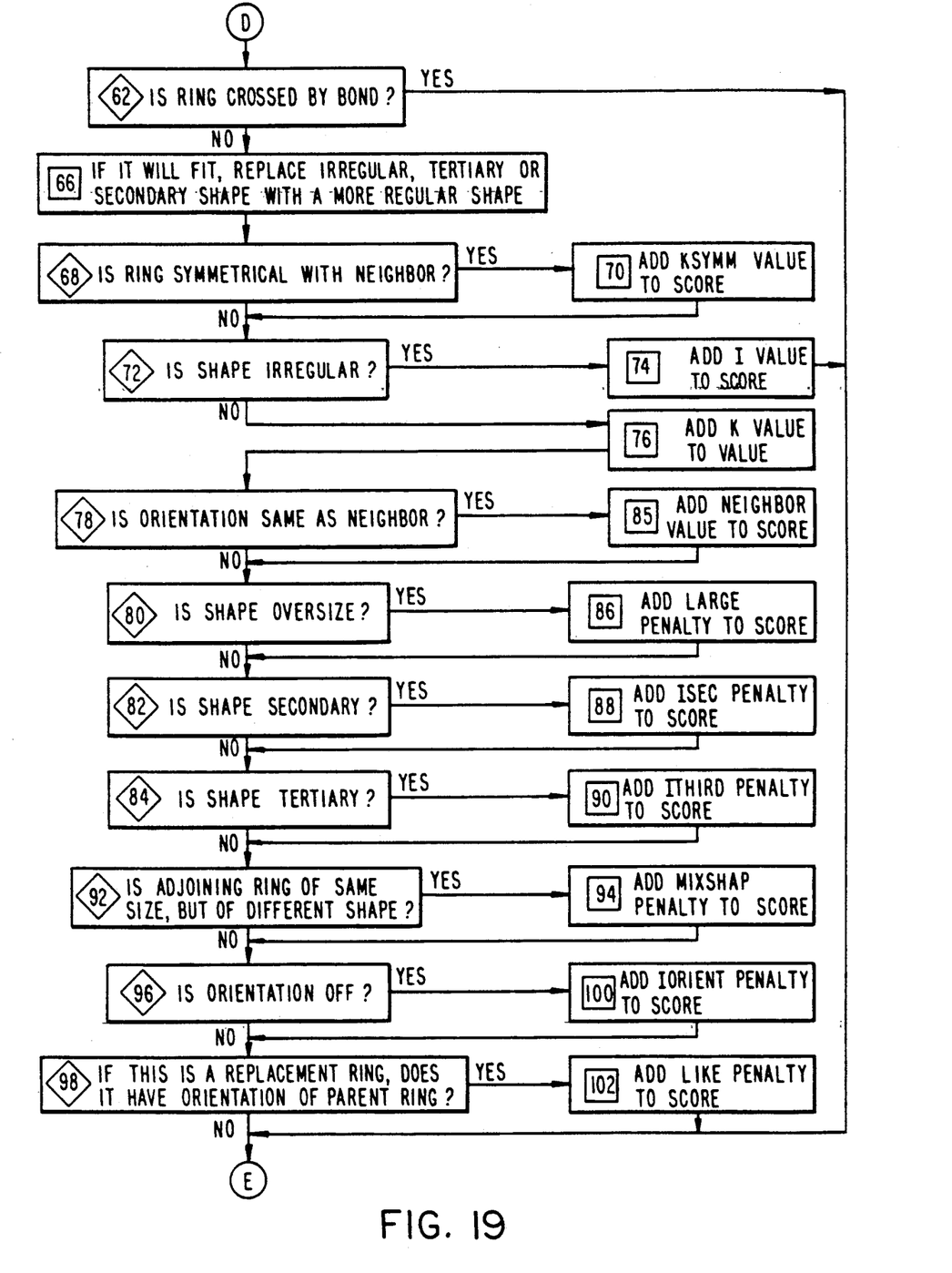

The first phase of the method has established and entered into memory the score of the distorted input structure 1. The process next proceeds to 56 in FIG. 18. At this point there begins an analysis of the alternate structures which can be developed as equivalents. The SAMPLE is now incremented by 1 to identify the first of the available alternate structures. A ring in the structure is now addressed at 60. Inquiry is made at 62 as to whether the ring is crossed by a bond. If the answer is affirmative an inquiry is made at 64 (FIG. 18) as to whether the ring is the last ring in the cluster to be examined. If the response is negative the next ring in the structure is examined at 60 and the "ring crossed by bond" inquiry again made at 62 (FIG. 19). When this question is answered in the negative an attempt is made at 66 to replace irregular, tertiary or secondary shapes with a more regular shape of the same size if a fit can be obtained. If this can be done the inquiry is then made as to whether the ring is symmetrical with its neighbor at 68. If the answer is affirmative the KSYMM value is added to the score at 70. Inquiry is next made as to the regularity or irregularity of the shape of the ring, at 72. If the ring is irregular, the appropriate I value from the table is added to the score at 74. If the shape is regular, the K value is credited to the score at 76. The orientation inquiry is made at 78, oversize inquiry at 80, secondary or tertiary inquiries at 82 and 84 and the appropriate NEIGHBOR, LARGE, ISEC and ITHIRD penalty or value added to the score at 85, 86, 88 and 90. At 92 the inquiry is made as to whether the adjoining ring is of the same size but different shape and the MIXSHAP penalty added at 94 if affirmative. Orientation is queried at 96 and relative orientation at 98 with the IORIENT penalty and LIKE value added at 100 and 102. Inquiry is again made at 64 (FIG. 18) as to whether the ring examined was the last ring in the alternate structure to be processed. In the affirmative, an inquiry is made in 104 to determine whether another path is avoidable for traversing the cluster. The values for the various structures examined and scored pursuant to this methodology are then compared at 106 and the sample with the highest score selected for output or printing. It will be appreciated that this method permits not only the restoring of original appearance but the improvement of such appearance.

Having now generally described this invention, the same will be better understood by reference to certain specific examples, which are included herein for purposes of illustration only and are not intended to be limiting of the invention or any embodiment thereof, unless so specified.

EXAMPLE 1

| | |
|---|---|
| Structure 1: | score: 4325 |
| K5 + ISEC | |
| K6 + IORIENT | |
| K6 | |
| K5 + NEIGHBOR | |
| I6 + MIXSHAP | |
| Structure 2: | score: 6025 |
| K5 | |
| K6 + NEIGHBOR | |
| K6 + LIKE + NEIGHBOR | |
| K5 + LIKE + NEIGHBOR | |
| K6 + KSYMM + NEIGHBOR | |

EXAMPLE 2

| | |
|---|---|
| Structure 1: | score: 1500 |
| I4 | |
| I5 | |
| I5 | |
| I6 | |
| K8 | |
| Structure 2: | score: 2850 |
| I4 | |
| K5 | |
| K5 + KSYMM + NEIGHBOR | |
| I6 | |
| I8 | |
| Structure 3: | score: 2150 |
| K4 | |
| K5 + NEIGHBOR | |
| I5 | |
| I6 | |
| I8 | |
| Structure 4: | score: 2150 |
| I4 | |
| I5 | |
| I5 + KSYMM | |
| K6 + LARGE | |
| I8 | |

EXAMPLE 3

| | |
|---|---|
| Structure 1: | score: 4675 |
| K4 + ITHIRD + NEIGHBOR | |
| K6 + ITHIRD | |
| K6 + ITHIRD + IORIENT + NEIGHBOR | |
| K6 + ITHIRD + NEIGHBOR | |
| K6 + ITHIRD + IORIENT + NEIGHBOR | |
| Structure 2: | score: 4050 |
| I4 | |
| K6 + KSYMM | |
| I6 + MIXSHAP + MIXSHAP | |
| K6 + NEIGHBOR | |
| K6 + KSYMM + NEIGHBOR | |

EXAMPLE 4

| | |
|---|---|
| Structure 1: | score: 3550 |
| K4 + ITHIRD | |
| K6 + ITHIRD + NEIGHBOR | |
| K6 + ITHIRD + NEIGHBOR | |
| K6 + ITHIRD + IORIENT | |
| Structure 2: | score: 4302 |
| I4 | |
| K6 + LIKE | |
| K6 + LIKE + NEIGHBOR + KSYMM | |
| K6 + NEIGHBOR + KSYMM | |

EXAMPLE 5

| | |
|---|---|
| Structure 1: | score: 1875 |
| K5 + ISEC + MIXSHAP | |
| K5 + LARGE | |
| I6 | |
| Structure 2: | score: 1900 |
| I5 | |
| I5 + KSYMM | |
| K6 + LARGE | |

EXAMPLE 6

| | |
|---|---|
| Structure 1: | score: 1525 |
| K6 | |
| I6 + MIXSHAP | |
| I6 | |
| Structure 2: | score: 2001 |
| I6 | |
| I6 + KSYMM | |
| K6 + LARGE + LIKE | |

EXAMPLE 7

| Structure 1: | score: 2800 |
|---|---|
| K4 | |
| I4 | |
| K5 + NEIGHBOR | |
| K6 + NEIGHBOR | |
| Structure 2: | score: 3052 |
| K4 + LIKE | |
| K4 + NEIGHBOR | |
| K5 + IORIENT | |
| K6 + NEIGHBOR + LIKE | |

EXAMPLE 8

| Structure 1: | score: 2800 |
|---|---|
| K4 | |
| I4 | |
| K5 + NEIGHBOR | |
| K6 + NEIGHBOR | |
| Structure 2: | score: 3302 |
| K4 | |
| K4 + KSYMM + IORIENT | |
| K5 + NEIGHBOR + LIKE | |
| K6 + NEIGHBOR + LIKE | |

The invention may be embodied in other specific forms without departing from the spirit or essential characteristics thereto. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

I claim:

1. A computer operated method for transforming a first chemical structure's appearance, comprising
   storing within a computer information representative of a series of parameters applicable to chemical structures, and values corresponding to the parameters;
   entering a first chemical structure into the computer as a first array;
   establishing which of the stored parameters are present in the first chemical structure and operating on the values present therein to establish a first score; and
   printing the structure corresponding to the first score.

2. The method of claim 1, wherein the first array is entered into the computer via a keyboard.

3. The method of claim 1, further comprising
   generating within the computer at least one alternate array representative of at least one alternate equivalent of the first structure;
   establishing which of the stored parameters are present in the alternate equivalent and operating on the values present therein to establish a score for the alternate equivalent;
   comparing the first score and the alternate score and selecting the highest one; and
   printing the structure corresponding to the thus obtained highest score if it is other than the first structure.

4. The method of claim 3, wherein establishing which of the parameters are present in the first structure or in an alternate equivalent thereof includes establishing whether any detected ring is
   symmetrical with a neighboring ring;
   of regular or irregular shape;
   oriented similar to a neighboring ring;
   of an oversized shape;
   of a secondary shape; or
   of a tertiary shape.

5. The method of claim 3, wherein
   more than one alternate array representative of more than one alternate equivalent of the first structure are generated within the computer; and
   their corresponding structures are compared.

6. The method of claim 3, further comprising prior to the score comparing step
   establishing whether the alternate equivalent includes one or more irregular tertiary or secondary shapes which can be replaced with a more regular shape of the same size and, if so, effecting such replacement in the alternate equivalent.

7. A method of claim 6, wherein the parameters comprise
   ring regularity;
   ring irregularity;
   ring secondary shape;
   ring tertiary shape; and
   symmetry.

8. The method of claim 7, wherein
   positive values are established for any regular and irregular rings of 3–8 members present in the structure; and
   negative values are established for any secondary and tertiary shapes present in the structure.

* * * * *